United States Patent [19]

Ishida et al.

[11] 4,388,215
[45] Jun. 14, 1983

[54] WOOD PRESERVATIVE COMPOSITION

[75] Inventors: Hideo Ishida; Masashi Kitada; Keisaku Ihara, all of Honjo, Japan

[73] Assignee: Sanyo Mokuzai Bofu Kabushiki Kaisha, Tokyo, Japan

[21] Appl. No.: 328,503

[22] Filed: Dec. 8, 1981

[30] Foreign Application Priority Data

Dec. 12, 1980 [JP] Japan .................................. 55-174711

[51] Int. Cl.³ .......................... B27K 3/40; C09K 15/14
[52] U.S. Cl. ....................................... 252/402; 162/160; 252/404; 427/440; 428/541; 428/907
[58] Field of Search ................ 252/402, 404; 162/160; 427/440; 428/541, 907

[56] References Cited

U.S. PATENT DOCUMENTS

| | | | |
|---|---|---|---|
| 3,452,038 | 6/1969 | Randall et al. | 162/160 |
| 4,288,249 | 9/1981 | Amundsen et al. | 427/440 |
| 4,290,846 | 9/1981 | Muntwyler | 427/440 |

*Primary Examiner*—Irwin Gluck

[57] ABSTRACT

A wood preservative composition comprising 2-mercaptobenzothiazole or its salt and 2,5-dichloro-4-bromophenol or its salt exerts an unexpected synergistic wood preservative effect against wood destroying fungi and termites.

5 Claims, No Drawings

WOOD PRESERVATIVE COMPOSITION

BACKGROUND OF THE INVENTION

This invention relates to a wood preservative composition capable of providing improved wood preservative performance in a wide variety of applications without giving rise to any toxic problem to human beings and animals.

Wood is one of the best structural materials for the construction of buildings because of increased specific strength, ease of processing, and relatively low cost. However, wood has one serious drawback that it is susceptible to decay by wood destroying fungi or attack by wood-worms, borers and termites. To eliminate this drawback, wood was traditionally treated with preservatives such as CCA (copper-chromium-arsenic system), PF (phenol-fluoride system), creosote oil and the like by pressure impregnation or immersion. In recent years, there is the need for wood preservatives which are free of heavy metals and safe for human beings and animals and do not cause pollution as public concern is directed to environmental pollution and hygienic influence. A variety of low-toxic wood preservatives have been proposed to meet such requirements.

Wood preservative compositions comprising the sodium salt of 2-mercaptobenzothiazole were proposed by the inventors as the most promising low-toxic wood preservatives as disclosed in Japanese Patent Application Kokai-Koho Nos. 54-151102 (Nov. 28, 1979), 54-151103 (Nov. 28, 1979), and 55-108805 (Aug. 21, 1980). Another wood preservative composition comprising 2,5-dichloro-4-bromophenol or its salt is described as being safe and effective in Japanese Patent Application Kokai-Koho No. 53-26303 (1978). However, 2,5-dichloro-4-bromophenol is relatively expensive.

In general, wood preservatives are used under widely varying conditions. The results of laboratory performance tests often deviate from the results obtained when preservatives are actually applied in the field.

The inventors have researched on possible actual application of these low-toxic wood-preservatives by comparing their effectiveness with conventional preservatives such as CCA and creosote oil which are highly effective in preservation, but giving rise to hygienic and pollution problems. The inventors have found that the above-mentioned two tapes of preservative compositions may be actually used in particular applications without causing any significant problems. However, this means that these preservative compositions are not satisfactory in every application. The inventors have found that 2-mercaptozenzothiazole or its salt and 2,5-dichloro-4-bromophenol have different fungicidal spectra, are distributed in different areas when applied to wood, and exert their maximum effect at different points of time after application to wood, and that by using these two compounds in admixture, not only an additive effect is obtained where one compensates for the shortcomings of the other, as is usual with the mixing of two different fungicides, but an unexpected synergistic effect is also obtained.

SUMMARY OF THE INVENTION

Accordingly, the present invention provides a wood preservative composition which comprises 2-mercaptobenzothiazole or its salt and 2,5-dichloro-4-bromophenol or its salt as active ingredients.

It has been found that 2-mercaptobenzothiazole and its salts are highly effective in preserving wood at or near the cut end and in regions remote from the ground and particularly provides excellent durability under initial severe environmental variations, that 2,5-dichloro-4-bromophenol and its salts provide wood with increased durability at the interior, prevent wood destroying fungi from invading the interior of the wood even when the surface portion has become rotten, and keep their effectiveness over a prolonged period of time, and that when these two compounds are used together, the resulting preservative effect is raised to the level which cannot be expected from the applications of these compounds alone.

DESCRIPTION OF THE PREFERRED EMBODIMENTS

The salts of 2-mercaptobenzothiazole used in the present invention include salts of metals, for example, alkali metals such as sodium and potassium, alkaline earth metals such as magnesium and calcium, and other metals such as copper and zinc; ammonium salt; and salts of amines for example, aliphatic amines, such as unsubstituted and substituted alkyl amines, typically 3-methoxy-propyl amine and 2-hydroxyethyl amine. Among these, the alkali metal salts, alkaline earth metal salts, ammonium salt, and amine salts are soluble in water. On the other hand, 2-mercaptobenzothiazole and its salts with metals other than alkali and alkaline earth metals, for example, copper and zinc salts are substantially insoluble in water.

The salts of 2,5-dichloro-4-bromophenol used herein include alkali metal salts, alkaline earth metal salts, ammonium salt, and amine salts as exemplified for the 2-mercaptobenzothiazole salts.

The composition generally contains 1 to 10 parts by weight of 2-mercaptobenzothiazole or its salts and 10 to 1 parts by weight of 2,5-dichloro-4-bromophenol or its salts. The preferred ratio of 2-mercaptobenzothiazole to 2,5-dichloro-4-bromophenol ranges from 2:1 to 5:1. This effective range is also preferred for cost reduction because 2,5-dichloro-4-bromophenol is relatively expensive.

In the practice of the present invention, 2-mercaptobenzothiazole, 2,5-dichloro-4-bromophenol and their salts may be in the form of solution, suspension, emulsion, paste or the like by usual preparation processes using water or organic solvents. In the case of the water-soluble salts, solutions may readily be prepared by dissolving the salts in water. The water-soluble salts are the most preferred as the active ingredient according to the present invention. However, water-insoluble ingredients, for example, 2-mercaptobenzothiazole and the other metal salts thereof described above may also be employed in the present invention. These water-soluble ingredients may be prepared into emulsion using water and suitable surface-active agents. Organic solvents may also be used, for example, methanol, ethanol, isopropyl alcohol, chloroform, dimethylformamide, n-hexane, dioxane, benzene, toluene, xylene, ethyl ether and the like.

The wood preservative composition according to the present invention may further include a conventional well-known preservative agent and/or any desired adjuvant. The wood preservative composition may be applied to any types of wood material including bamboo, plywood panels and particle boards. This composition is also effective as a soil treating agent.

In order that those skilled in the art will more fully understand how to practice the present invention, examples of the present invention are set forth below by way of illustration and not by way of limitation. All percentages are by weight.

| Example 1 | |
| --- | --- |
| 2-Mercaptobenzothiazole | 0.6% |
| 2,5-Dichloro-4-bromophenol | 0.3% |
| Dimethylformamide | 10% |
| Xylene | 89.1% |
| Example 2 | |
| Sodium 2-mercaptobenzothiazole | 0.5% |
| 2,5-Dichloro-4-bromophenol | 0.3% |
| Sodium sulfite | 0.5% |
| Water | 98.7% |
| Example 3 | |
| Ammonium 2-mercaptobenzothiazole | 0.7% |
| Sodium 2,5-dichloro-4-bromophenol | 0.2% |
| Sodium sulfite | 0.5% |
| Water | 98.6% |
| Comparative Example 1 | |
| 2-Mercaptobenzothiazole | 1% |
| Dimethylformamide | 10% |
| Xylene | 89% |
| Comparative Example 2 | |
| Sodium 2,5-dichloro-4-bromophenol | 1% |
| Water | 99% |
| Comparative Example 3 | |
| Sodium 2-mercaptobenzothiazole | 1% |
| Sodium sulfite | 1% |
| Water | 98% |

In each Example, the above-mentioned ingredients were mixed into a homogeneous mixture.

TEST 1

Wood was treated with each of the wood preservative compositions prepared in Examples 1-3 and Comparative Examples 1-3. A first group designated A included 10 timbers of hemlock spruce (10.5×10.5×100 cm) to which each of the preservative compositions was applied to a concentration of 200 g/m$^2$. A second group designated B included 10 logs of Japan cedar (diameter 10 cm, length 100 cm) which were pressure impregnated with each of the preservative compositions to a concentration of 300 kg/m$^3$. A third group designated C included 10 timbers of hemlock spruce (10.5×10.5×100 cm) which were pressure impregnated with each of the preservative compositions to a concentration of 300 kg/m$^3$. The timbers of group A were horizontally placed on the ground whereas the logs and timbers of groups B and C were vertically stood on the ground with their lower half embedded in the ground. After three years, the timbers and logs were examined for decay and termite attack. The results are shown in Table 1. The degree of decay and attack shown in Table 1 is an average of ten measurements which are on the basis of the following criteria.

| Degree of decay and attack | Observation |
| --- | --- |
| 0 | no change |
| 1 | partial light attack or decay |
| 2 | overall light attack or decay |
| 3 | partial heavy attack or decay in addition to overall light attack or decay |
| 4 | overall heavy attack or decay |
| 5 | ruin by attack or decay |

TABLE 1

| | Average degree of decay and attack | | | | | |
| --- | --- | --- | --- | --- | --- | --- |
| | Group A | | Group B | | Group C | |
| Preservative | Ground side | Upper side | Underground | Aboveground | Underground | Aboveground |
| Example 1 | 0 | 0 | — | — | — | — |
| Example 2 | 0.1 | 0 | 0 | 0 | 0 | 0 |
| Example 3 | 0 | 0 | 0 | 0 | 0 | 0 |
| Comparative Example 1 | 2.1 | 0.2 | — | — | — | — |
| Comparative Example 2 | 2.9 | 1.1 | 2.3 | 1.2 | 1.5 | 1.0 |
| Comparative Example 3 | 1.7 | 0.7 | 3.0 | 0.2 | 2.2 | 0.1 |
| Control | 4.8 | 1.8 | 4.8 | 2.0 | 4.9 | 2.9 |

As seen from the data of Table 1, the wood preservative compositions of the present invention exert an unexpectedly increased wood preservative effect. The use of combinations of 2-mercaptobenzothiazole and 2,5-dichloro-4-bromophenol are highly effective over the use of each compound when the total amount of the former is the same as in the case of single use. This means that the total amount of a combination of the two compounds may be reduced as long as an acceptable effect is obtained.

TEST 2

Samples of wood were treated with 2-mercaptobenzothiazole alone, 2,5-dichloro-4-bromophenol alone, and a mixture of 2-mercaptobenzothiazole and 2,5-dichloro-4-bromophenol. To obtain substantially equal wood preservative effect against house termite (*Coptotermes formosana*) and Japan termite (*Reticulitermes speratus*), the following concentrations of the respective agents were needed.

TABLE 2

| | MBT* | DCBP** | MBT + DCBP | |
| --- | --- | --- | --- | --- |
| *Coptotermes formosana* | 10% | 0.5% | 0.4% | 0.1% |
| *Reticulitermes speratus* | 1% | 0.5% | 0.3% | 0.06% |

*2-mercaptobenzothiazole
**2,5-dichloro-4-bromophenol

As seen from the data of Table 2, the use of MBT in admixture with DCBP is substantially advantageous in application amount and cost over the use of the respective agents. Such a synergistic effect is quite unexpected.

What is claimed is:

1. A wood preservative composition comprising 2-mercaptobenzothiazole or its salt and 2,5-dichloro-4-bromophenol or its salt.

2. A wood preservative composition according to claim 1 wherein 2-mercaptobenzothiazole or its salt is present in an amount of 1 to 10 parts by weight and 2,5-dichloro-4-bromophenol or its salt is present in an amount of 10 to 1 parts by weight.

3. A wood preservative composition according to claim 1 wherein 2-mercaptobenzothiazole or its salt is present in an amount of 2 to 5 parts by weight per part of 2,5-dichloro-4-bromophenol or its salt.

4. A wood preservative composition according to claim 1 wherein the 2-mercaptobenzothiazole salt is selected from the group consisting of alkali metal salts, alkaline earth metal salts, ammonium salt and amine salts of 2-mercaptobenzothiazole.

5. A wood preservative composition according to claim 1 wherein the 2,5-dichloro-4-bromophenol salt is selected from the group consisting of alkali metal salts, alkaline earth metal salts, ammonium salt and amine salts of 2,5-dichloro-4-bromophenol.

* * * * *